US00PP09200P

United States Patent [19]

Pitman

[11] Patent Number: Plant 9,200

[45] Date of Patent: Jul. 18, 1995

[54] IXORA PLANT NAMED FRANKIE HIPP

[75] Inventor: Fabia C. Pitman, Homestead, Fla.

[73] Assignee: Patricia A. Button, Coral Gables, Fla.

[21] Appl. No.: 314,392

[22] Filed: Sep. 28, 1994

[51] Int. Cl.[6] ..... A01H 5/00

[52] U.S. Cl. ..... Plt./54.1

[58] Field of Search ..... Plt. 54.1

*Primary Examiner*—James R. Feyrer

*Attorney, Agent, or Firm*—Foley & Lardner

[57] ABSTRACT

A new and distinct Ixora plant named Frankie Hipp characterized by its large inflorescences, white flowers having thin pink margins, its large number of flower and buds per inflorescence, and its relatively slow growing habit.

2 Drawing Sheets

The present invention comprises a new and distinct cultivar of Ixora, botanically known as *Ixora coccinea,* and referred to by the cultivar name Frankie Hipp.

The new cultivar is a spontaneous mutation discovered by the inventor Fabia C. Pitman in Homestead, Fla. in Sep. 1989. The new cultivar was discovered in a cultivated planting of the parent cultivar *Ixora coccinea* Nora Grant, and was recognized by its white flower color, a clear contrast to the rose red flower color of the parent.

Frankie Hipp was first propagated by the inventor in Sep. 1989 in Homestead, Fla. Propagation was by leaf cuttings which served not only to increase the number of plants for evaluation but to demonstrate the stability of the combination of characteristics from generation to generation.

The following observations, measurements and values describe plants grown in Homestead, Fla. under field conditions which closely approximate those generally used in horticulture practice.

The following traits have been repeatedly observed to be characteristics which in combination distinguish Frankie Hipp from the parent cultivar Nora Grant, an unpatented but commercially well-known plant.

1. Frankie Hipp has white flowers with a thin pink margin and occasional pink streaks on the petals, as contrasted to the general solid rose red flower color of Nora Grant.

2. The inflorescences of Frankie Hipp are larger and contain more flowers than Nora Grant.

3. The flower petals are less reflexed than those of Nora Grant.

4. Frankie Hipp is a slower growing plant than Nora Grant.

All color references noted below are measured against The Royal Horticultural Society Colour Chart. Colors are as closely approximate as possible, but it will be understood that color depends to some extent on horticultural practices such as light level and fertilization rate, among others, without, however, any variance in genotype.

The color photographic drawings illustrate the new cultivar, with the photo on Sheet 1 being a top perspective view of the inflorescence and foliage of Frankie Hipp, and the photo on Sheet 2 illustrating in more detail the flowers of Frankie Hipp.

The photograph comprising Sheet 1 is of a plant of Frankie Hipp in a 25.5 cm pot approximately six months after planting three rooted four-leaf cuttings, and grown under appropriate growing conditions.

The photographic colors are as accurate as possible with color illustrations of this type.

The closest comparison cultivar is the parent Nora Grant. The differences between the respective cultivars are noted above and are set forth in greater detail in attached CHART A. There are a number of differences, the most important of which are the substantially larger inflorescence and the white flower color with pink margins.

Origin: Mutation discovered among cultivated plants of *Ixora coccinea,* cv. Nora Grant.

Classification: *Ixora coccinea,* cv. Frankie Hipp.

Propagation: Asexual reproduction by leaf cuttings.

Plant: A plant grown in a 25.5 cm pot from three rooted four-leaf cuttings will reach a mature size, after six months under appropriate growing conditions, of approximately 58 cm to 60 cm in height and approximately 40 cm to 65 cm in width.

Leaves:

*Form.*—The leaves are paired and opposite along the stem, and pairs are spaced approximately 2.5 cm to 5.6 cm apart. The leaf blade is elliptic with an acute tip and an obtuse base. The margins are entire. The leaf surface is leathery and glossy. The midrib protrudes from the upper and lower surfaces of the leaf, and is straight over the length of the leaf. The leaf blade tends to be cupped or folded upward from the midrib.

*Size.*—Leaf blades of a mature-sized plant are approximately 8.0 cm to 10.5 cm in length and approximately 4.6 cm to 5.5 cm in width. The petiole is approximately 4 mm in length, and 3 mm thick.

*Veins.*—Primary veins protrude slightly from the upper and lower surfaces, with the leaf blade slightly recessed between veins on the upper surface. There are approximately 14 primary veins on the leaf. The veins are the same color as the surrounding tissue.

*Color.*—Upper surface: New, 144A; mature, darker and greener than, but closest to, 139A. Lower surface: New, 146D; mature, 146B. Midrib (upper surface): New, 144B; mature, 146B. Midrib (lower surface): New, 144B; mature, 146C. New foliage typically becomes anthocyanous when exposed to strong direct lighting.

Flowers:

*Borne.*—The flowers are produced in branched, crowded terminal corymbs.

*Shape of inflorescence.*—Compact globose clusters.

*Individual flowers.*—Corolla gamopetalous, salverform, comprising a tube and an expanded limb having four (4) expanded lobes or petals. Calyx is inconspicuous, comprising four (4) triangular sepals — 1.2 mm long, 1 mm wide, and 144B in color.

*Time of blooming.*—The plants flower year round in warm climates, with peak flowering occurring during the summer months.

*Duration of bloom.*—Individual flowers remain open for approximately five (5) days before senescing.

Reproductive organs:

*Pistil.*—The stigma is bifurcate, each lobe reflexed back, color 50B; the style is approximately 3.6 cm long, 0.1 mm in diameter and 145C in color. The ovary is inferior, 2 mm in length and thickness, and 144A in color.

*Stamens.*—Four (4) present, affixed to the junction of the tube and the limb; 3 mm in length and 0.9 mm in width; color 14C.

CHART A

| Characteristic | Frankie Hipp | Nora Grant |
|---|---|---|
| Limb Color | | |
| Upper Surface | | |
| New | 155D with 50A-B margin | 51B |
| Faded | 19C with 50A margin | 50A |
| Under Surface | | |
| New | 155D with 50A-B margin | 51D |
| Faded | 19C with 50A margin | 51D |
| Tube | | |
| Length | Approx. 3.0 cm | 3.0 cm |
| Diameter | Approx. 1.1 mm | 1.1 mm |
| Color | 150D | Greener, but closest to 50C |
| Flower (Limb) Diameter | 2.5–2.9 cm | 2.5–2.9 cm |
| Lobe (Petal) Width | 8–9 mm | 6–8 mm |
| Diameter of inflorescence | 9–14 cm | 7–10 cm |
| Quantity of flower and buds per inflorescence | 77–156 | 60–75 |

The foregoing is based on the growing of a representative number of plants of each cultivar under identical conditions at Homestead, Fla.

It is claimed:

1. A new and distinct cultivar of Ixora plant named Frank Hipp, as illustrated and described.

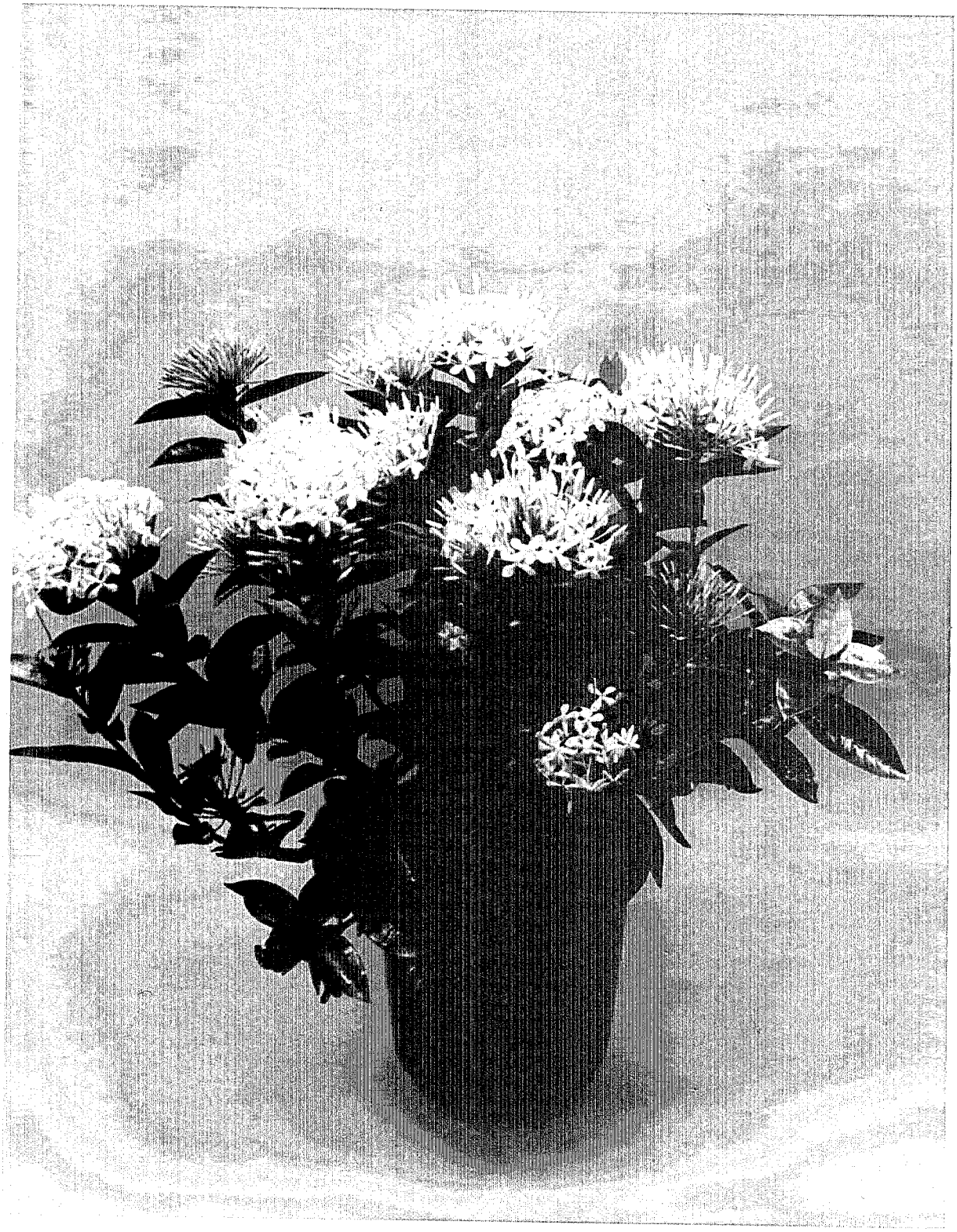

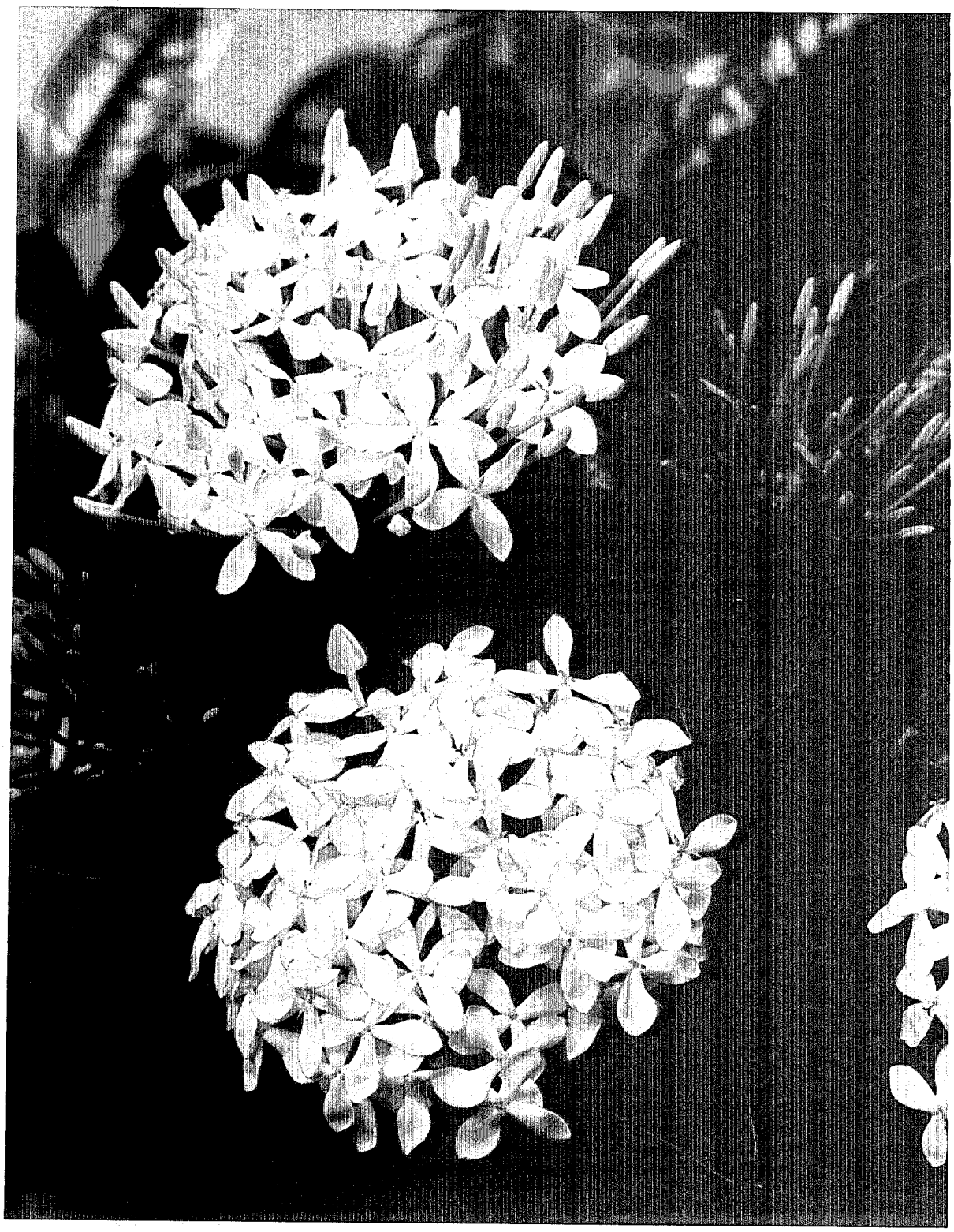

* * * * *